United States Patent [19]

Key et al.

[11] Patent Number: 5,244,787
[45] Date of Patent: Sep. 14, 1993

[54] ANTIGEN RETRIEVAL IN FORMALIN FIXED TISSUES USING MICROWAVE ENERGY

[75] Inventors: Marc E. Key, Navato; Shan-Rong Shi, San Ramon; Krishan L. Kalra, Danville, all of Calif.

[73] Assignee: Biogenex Laboratories, San Ramon, Calif.

[21] Appl. No.: 649,036

[22] Filed: Jan. 31, 1991

[51] Int. Cl.$^5$ ............... C12Q 1/00; G01N 33/535
[52] U.S. Cl. ............................ 435/7.9; 424/3; 435/7.94; 435/7.92; 436/518; 436/519
[58] Field of Search ............... 424/3; 435/7.9, 7.94; 436/518

[56] References Cited

U.S. PATENT DOCUMENTS 4,656,047  4/1987  Kok et al. ........................... 424/3
4,839,194  6/1989  Malluche et al. .................. 424/3

OTHER PUBLICATIONS

"Antigen preservation in microwave irradiated tissues: A comparison with formaldehyde fixation" by A. S. -Y. Leong, et al., in *Journal of Pathology*, 156:275-282 (1987).
"Histological fixation by microwave heating" by C. P. Mayers, in *J. Clin. Pathol.*, 23:273-275 (1970).
"Microwave fixation: Its potential for routine techniques, histochemistry, immunocytomchemistry and electron microscopy" by D. Hopwood, et al., in *Histochem. J.*, 16:1171-1191 (1984).
"Microwave energy fixation for electron microscopy", by G. R. Login and A. M. Dvorak, in *Am. J. Pathol.*, 120:230-243 (1985).
"Use of Microwaves for acid and alcohol fast staining" by S. Hafiz, et al., in *J. Clin. Path.*, 38:1073-1084 (1985).
"Selected enzyme histochemical techniques facilitated by the microwave oven" by N. Brinn and W. Terrell, in *J. Histotechnology*, 9:231-234 (1986).
"Special stains in the microwave oven" by S. Valle, in *J. Histotechnology*, 9:237-239 (1986).
"Use of microwaves for rapid immunoperoxidase staining of paraffin sections" by K. Y. Chiu, in *Med. Lab. Sci.*, 44:3-5 (1987).
"BrdUrd labeling of S-phase cells in testes and small intestine of mice, using microwave irradiation for immunogold-silver staining: An immunocytomchemical study" by B. Thoolen, in *J. Histochem. Cytochem.*, 38:267-273 (1990).
"Improved immunoperoxidase staining using microwave slide drawing" by H. M. Sharma, et al., in *Laboratory Medicine*, 21:658-660 (1990).
"Zinc formalin fixative for automated tissue processing" by Gilbert E. Herman, et al., in *Journ. of Histol.*, 11:2 (1988).
"Immunohistologic techniques in surgical pathology—a spectrum of new special stains" by C. R. Taylor, M.D., et al., in *Perspectives of Path.*, 12:7 (1981).
"Transition Metal Sacts as Adjuncts to Formalin for Tissue Fixation" by M. J. Jones, et al., in *Laboratory Investigation*, 44:32A (1981).
"Enhancement of Immunoreactivity in Paraffin Embedded Tissues by Refixation in Zinc Sulfate-Formalin", S. L. Abbondanzo, et al., *The United States and Canadian Academy of Pathology, Inc.*, (1990).
"Diagnostic immunohistochemistry in tumor pathology: an overview" by R. A. DeLellis, M.D., in *Diagnostic Immunohistochemistry*, (See Specification pp. 3-5).
"A rapid method of staining ultrathin sections of surgical pathology TEM with the use of the microwave oven" by J. C. Estrada, et al., *Dept. of Pathol.*, 83:5 (1984).

(List continued on next page.)

Primary Examiner—Sam Rosen
Attorney, Agent, or Firm—Cooley Godward Castro Huddleson & Tatum

[57] ABSTRACT

A method of immunologically staining a formalin-fixed tissue preparation, which comprises (a) subjecting a formalin-fixed tissue preparation to microwave energy while the tissue preparation is submersed in water for a time sufficient to increase immunostaining efficiency; (b) removing the tissue preparation from the water and cooling; and (c) contacting the tissue preparation with an immunological staining reagent.

18 Claims, No Drawings

OTHER PUBLICATIONS

"Cross-linking of amino acids by formaldehyde. Preparation and 13C NMR spectra of model compounds" by D. P. Kelly, et al., *Dept. of Organic Chem.*

"Chemistry of the crosslinking of collagen during tanning" by J. W. Harlen and S. H. Feairheller.

"Formaldehyde fixation" by C. H. Fox, et al., in *Journ. of Histochemistry and Cytochemistry*, 33:845–853 (1985).

"Application of immunofluorescent staining on paraffin sections improved by trypsin digestion" by Shao-nan Huang, et al., in *International Academy of Pathology*, 35:383 (1976).

"The influence of protease digestion and duration of fixation on the immunostaining of keratins" by Hector Battifora and Mary Kopinski in *Journ. of Histochemistry and Cystochemistry*, 34:1095–1100 (1986).

"Formaldehyde sensitivity of a GFAP Epitope, Removed by Extraction of the Cytoskeleton With High Salt" by P. B. Bell, Jr. et al., in *Journ. of Histochemistry and Cytochemistry*, 35:1375–1380 (1987).

"Comparative effect of microwaves and boiling on the denaturation of DNA" by William G. Stroop and Douglas C. Schaefer, in *Analytical Biochemistry*, 182:222–225 (1989).

"Quantitive assessment of cellular changes provoked by microwave enhanced fixation of parathyroids" by P. Wild and E. M. Schraner in *Histochemistry*, 92:69–72 (1989).

"The distribution of vimentin and keratin in epithelial and nonepithelial neoplasms" by Norio Azumi and Hector Battifora, M.D. in *Sylvia Cowan Laboratory of Surgical Pathology*, 88:286–296 (1986).

"Aminoacid Isomerisation and Microwave Exposure", G. Lubec, et al., *The Lancet*, pp. 1392–1293 (1989).

ANTIGEN RETRIEVAL IN FORMALIN FIXED TISSUES USING MICROWAVE ENERGY

TECHNICAL FIELD

This application is directed to the field of tissue staining and is particularly directed to antibody-directed staining of formalin-fixed tissue

BACKGROUND

Growing interest in immunohistochemical staining procedures has led to the development of a wide range of highly specific immunostains which are of value to the surgical pathologist in diagnostic and investigative studies (1, 2). Although formalin remains the most popular fixative used in pathology, it is clear that this fixative is not always the best choice for preserving antigenicity of tissues to be used in immunohistochemical procedures Despite numerous studies on the intermolecular crosslinks formed between formalin and proteins (3, 4), the molecular mechanism underlying tissue fixation is not well understood (5).

The demand for a broader selection of antibodies which can be used for immunohistochemical staining on routine formalin-fixed, paraffin-embedded tissues has stimulated efforts to develop antibodies which can recognize formalin-resistant epitopes Although this strategy has been effective in developing many useful antibodies, it has not been entirely satisfactory in resolving all problems. A persistent concern in immunopathology is choosing the correct fixative and duration of fixation that will provide the maximum preservation of tissue morphology with minimum loss of antigenicity.

One approach to resolve this dilemma was the introduction of protease digestion of formalin-fixed sections to unmask antigenic sites hidden by cross-linked proteins (6, 7). However, Leong, et al , (8) showed that, aside from cytokeratins and desmin, digestion with trypsin did not improve immunostaining of the other antigens studied. Presently it is not clear whether or not the formalin-induced cross-linking of proteins is a reversible chemical reaction. However, a recent study concerning formalin sensitivity of a GFAP epitope supported the hypothesis that the sensitivity of some epitopes was not due to the direct effect of the aldehyde, but rather due to the binding of other molecular structures to the epitope (9).

Clearly the ability to bind immunostaining reagents with epitopes masked by formalin fixation (referred to here as antigen-retrieval) could significantly expand the range of antibodies useful in immunohistochemistry as well as reduce the incidence of false negative staining in over-fixed tissues. Additionally, antigen retrieval could provide greater diagnostic accuracy by improving immunohistochemical procedures. With these goals in mind we studied the effects of microwave oven heating of tissue sections in the presence and absence of metal solutions. The dramatic enhancing effect of this treatment on antigen recovery and immunohistochemical staining was particularly surprising considering the deleterious effects that high temperatures are presumed to have on protein antigens.

The microwave oven has previously been used for tissue fixation (8, 10, 11) and for rapid histochemical and immunohistochemical staining (12-19). One recent report has also observed enhanced immunohistochemical staining following microwave drying of slides (20). However, in these cases, only short periods of irradiation and low temperatures were used To the best of our knowledge, no one has previously accomplished antigen retrieval by the use of the microwave oven alone or with metal solutions. Similarly, no studies have indicated that immunohistochemical staining intensity could be increased by heating slides in water with microwaves to temperatures of approximately 100° C.

The use of heavy metal salts in combination with formalin for tissue fixation has recently been introduced (21, 22). Some studies have demonstrated the superiority of zinc formalin as a fixative for antigen preservation (22) Furthermore, when routine formalinfixed tissues were re-fixed in zinc formalin, immunoreactivity was improved (23).

Although little has been published on the molecular changes in amino acids and other compounds that occur after microwave treatment (24), Stroop, et al., (25) demonstrated that microwave treatment of radiolabeled DNA probes allowed these probes to be diluted about 20 times more than when these probes were denatured by conventional heat.

Relevant Literature

1. Taylor, C. R. and Kledzik, G., "Immunohistologic techniques in surgical pathology—A spectrum of "new" special stains", *Hum. Pathol.* (1981), 12:590-596.
2. DeLellis, R. A., "Diagnostic Immunohistochemistry", New York, Paris, Barcelona, Milan, Mexico City, Rio de Janeiro, Masson Publishing USA, Inc. (1981), pp. 1-3.
3. Kelly, D. P., et al., "Crosslinking of amino acids by formaldehyde. Preparation and 13C NMR spectra of model compounds", *Protein Crosslinking*, Symposium on Protein Crosslinking, San Francisco, (1976), Edited by M. Friedman, New York, Plenum Press, 1977, pp. 641-647.
4. Harlan, J. W., and Feairheller, S. H., "Chemistry of the crosslinking of collagen during tanning", Ibid., pp. 425-440.
5. Fox, C. H., et al., "Formaldehyde fixation", *J. Histochem. Cytochem.* (1985), 33:845-853.
6. Huang, S. N., et al., "Application of immunofluorescent staining on paraffin sections improved by trypsin digestion", *Lab. Invest.* (1976), 35:383-390.
7. Battifora, H., and Kopinski, M., "The influence of protease digestion and duration of fixation on the immunostaining of keratins", *J. Histochem Cytochem.* (1986), 34:1095-1100.
8. Leong, A. S. Y., et al., "Antigen preservation in microwave-irradiated tissues: A comparison with formaldehyde fixation", *J. Pathol.* (1988), 156:275-282.
9. Bell, P. B., Jr., et al., "Formaldehyde sensitivity of a GFAP epitope, removed by extraction of the cytoskeleton with high salt", *J. Histochem. Cytochem.* (1987), 35:1375-1380.
10. Mayers, C. P., "Histological fixation by microwave heating", *J. Clin. Pathol.* (1970), 23:273-275.
11. Hopwood, D., et al., "Microwave fixation Its potential for routine techniques, histochemistry, immunocytochemistry and electron microscopy", *Histochem. J.* (1984), 16:1171-1191.
12. Login, G. R., and Dvorak, A. M., "Microwave energy fixation for electron microscopy", *Am. J. Pathol.* (1985), 120:230-243.

13. Brinn, N. T., "Rapid metallic histological staining using the microwave oven", *J. Histotechnol.* (1983), 6:125–129.
14. Estrada, J. C., et al., "A rapid method of staining ultrathin sections for surgical pathology-TEM with the use of the microwave oven", *Am. J. Clin. Pathol.* (1985), 83:639–641.
15. Hafiz, S., et al., "Use of microwaves for acid and alcohol fast staining", *J. Clin. Pathol.* (1985), 38:1073–1076.
16. Brinn, N., and Terrell, W., "Selected enzyme histochemical techniques facilitated by the microwave oven", *J. Histotechnol.* (1986), 9:231–234.
17. Valle, S., "Special stains in the microwave oven", *J. Histotechnol.* (1986), 9:237–239.
18. Chiu, K. Y., "Use of microwaves for rapid immunoperoxidase staining of paraffin sections", *Med Lab. Sci.* (1987), 44:3–5.
19. Thoolen, B., "BrdUrd labeling of S-phase cells in testes and small intestine of mice, using microwave irradiation for immunogold-silver staining: An immunocytochemical study", *J. Histochem Cytochem.* (1990), 38:267–273.
20. Sharma HM, Kauffman EM, McGaughy VR: "Improved immunoperoxidase staining using microwave slide drying," Lab. Medicine: 21: 658–660, 1990.
21. Jones, M. D., et al., "Transition metal salts as adjuncts to formalin for tissue fixation", Abstract, *Lab Invest* (1981), 44:32A.
22. Herman, G. E., et al., "Zinc formalin fixative for automated tissue processing", *J. Histotechnol.* (1988), 11:85–89.
23. Abbondanzo, S. L., et al., "Enhancement of immunoreactivity in paraffin embedded tissues by refixation in zinc sulfate-formalin", presented at the Annual Meeting of United States and Canadian Academy of Pathology, Boston, Mar. 4–9, 1990.
24. Lubec, G., et al., "Amino acid isomerization and microwave exposure", *Lancet* (1989), 11:1392–1393.
25. Stroop, W. G., and Schaefer, D. C., "Comparative effect of microwaves and boiling on the denaturation of DNA", *Anal. Biochem.* (1989), 182:222–225.
26. Wild, P., and Schraner, E. M., "Quantitative assessment of cellular charges provoked by microwave enhanced fixation of parathyroids", *Histochem* (1989), 92:69–72.
27. Azumi N, Battifora H., "The distribution of vimentin and keratin in epithelial and nonepithelial cells," *Am. J. Clin. Path.* (1987), 88:286–296.

SUMMARY OF THE INVENTION

It is an object of the present invention to provide an improved technique for immunological staining of formalin-fixed tissue.

It is particularly desirable to provide a technique that is generally applicable and which is simple to carry out with readily available equipment.

Accordingly, these and other objects of the invention as will hereinafter become more readily apparent by reference to the following detailed description of the invention have been accomplished by providing a method of immunologically staining a formalin-fixed tissue preparation, which comprises (a) heating a formalin-fixed tissue preparation using microwave energy while the tissue preparation is submersed in water, (b) removing the tissue preparation from the water and cooling, and (c) contacting the tissue preparation with an immunological staining reagent or series of reagents.

DESCRIPTION OF SPECIFIC EMBODIMENTS

The present invention provides a new approach for retrieval of antigens from formalin-fixed, paraffin-embedded tissues and their subsequent staining by immunohistochemical techniques. This method of antigen retrieval is based on microwave heating of tissue sections. The tissue sections are immersed in water and are preferably attached to microscope slides. Only moderate heating is required to improve immunostaining, but heating to temperatures sufficient to boil a solution of water, or plain water, in which the tissue preparation is submersed are preferred. This temperature is preferably at about 100° C. ($\pm 5°$ C.) and preferably takes place in the presence of metal ions.

Among 52 monoclonal and polyclonal antibodies tested by the method of the invention, 39 antibodies demonstrated a significant increase in immunostaining, nine antibodies showed no change, and four antibodies showed reduced immunostaining. In particular, excellent immunostaining results were obtained with monoclonal antibody to vimentin as well as several different keratin antibodies on routine formalin-fixed tissue sections after pre-treatment of the slides with this method. These results showed that antigen retrieval process of the invention has a number of useful properties: 1) enzyme pre-digestion of tissues is not necessary, 2) incubation times with primary antibodies can be significantly reduced and dilutions of primary antibodies can be increased, 3) adequate staining can be achieved in tissues fixed for from, e.g., two weeks up to two years in formalin which fail to stain by conventional methods, and 4) certain antibodies, which are typically unreactive with formalin-fixed tissues, give excellent staining using the techniques of the invention.

Although the method of the invention does not increase immunostaining for every antibody-antigen pair, as indicated by the statistics above the technique is none the less generally useful as it increases immunostaining in about ¾ of antibody-antigen pairs tested so far. Similar results are expected for other antibody-antigen pairs. Furthermore, whether immunostaining will be increased for any particular staining antibody can readily be determined on a small scale before being applied generally for use with a particular antibody. In other words, for each new antibody to be used in a staining process, the method of the invention is carried out and compared to immunostaining in the absence of microwave heating Detailed examples of how this process is carried out are set forth below. If immunostaining is increased, the process of the invention will be effective generally for that antibody-antigen pair in the future. The testing is straight forward and easily accomplished in about two hours, during which time several different antibodies can be tested concurrently.

Although the mechanism by which microwave oven recovery of antigens takes place is not clear (since this treatment did not affect alcohol-fixed paraffin sections), it is possible that the crosslinking of proteins caused by formaldehyde is altered by microwave heating. The morphology of tissues after microwave oven irradiation for 10 minutes showed no significant changes based on light microscopic analysis. However, some ultrastructural alterations, as suggested by a recent study (26), may be present resulting from fixing (rather than antigen recovery).

When compared to protease digestion, the influence of microwave pre-treatment was clearly superior, particularly in long-term formalin-fixed tissues. Particularly significant was our finding that tissues fixed in formalin for two weeks up to two years could still be immunostained following antigen retrieval even though enzyme pre-digestion failed to restore immunoreactivity.

A comparison between microwave oven treatment and conventional heating methods (conventional oven) showed significantly different immunostaining results. While pre-treating the slides to boiling (100°±5° C.) by microwave oven resulted in excellent immunostaining, poor results were obtained by pre-treating the slides with boiling water using conventional heat. It may be that some additional physical effects from microwave irradiation are important factors in achieving enhancement.

Furthermore, we found that the use of metal solutions in combination with microwave oven heating could substantially improve the immunoreactivity above that achievable with no treatment or microwave treatment in distilled water. This was particularly evident in tissues which had been fixed in formalin for greater than 24 hours. Some antibodies used in these studies could be diluted hundreds of times further than their usual concentrations. In addition, these antibodies could be used at their usual concentrations, but the incubation times of the antibody reaction on the tissues could be shortened by approximately 6-fold with no loss in sensitivity.

Different metal ions can be used in this preferred embodiment of the invention. Divalent metal ions are preferred, particularly divalent transition metals and group 4a metals, particularly tin and lead. Two particular preferred metal ions are zinc and lead. Lead ions are more effective than zinc during microwave oven treatment, since the lead solution demonstrated stronger immunoreactivity with less background.

The practice of the present invention is quite straightforward and requires no special equipment or formulations and no modification of previously used immunological staining techniques. The process is carried out on a formalin-fixed tissue preparation prepared by any fixing process that uses formalin (or a different formaldehyde derivative or form) as a tissue-fixing agent. Since the tissue preparation that is used in the present invention is prepared prior to the process of the invention, the preparation of such formalin-fixed, paraffin-embedded tissue samples is not part of the present invention and, in fact, is well known to those of ordinary skill in the art. An example is described below for purposes of illustration.

Additionally, certain steps can occur after fixing (and storage, if storage takes place) of the tissue preparation but prior to the microwave-heating process. Typically, paraffin is removed from the paraffin-embedded tissue, for example by melting of the paraffin (which has a melting point of approximately 55° C.–60° C. depending upon the type of paraffin) or dissolving the paraffin in an appropriate solvent, such as chloroform or xylene. If an enzyme label, such as horseradish peroxidase, is used as a label in the immunostaining process, background enzymatic activity can be reduced; for example, endogenous peroxidase can be blocked with a solution of hydrogen peroxide, after which excess hydrogen peroxide is washed from the tissue preparation. The tissue preparation, which is typically on a glass slide, is then placed in water or an appropriate aqueous solution for the microwave heating process.

Since the process of the present invention can take place either in water or in an aqueous solution (such as a buffered solution or a solution containing metal ions, as discussed below), this step of the process is generally referred to in this specification as placing the tissue preparation into "water" rather than the more cumbersome "water or an aqueous solution." Reference solely to "water" is therefore understood in this specification to indicate either water or an aqueous solution. If an aqueous solution is used, the solution will preferably be at least 90% $H_2O$ by weight, more preferably at least 95% $H_2O$, and most preferably at least 98% $H_2O$.

Although improved antigen recovery (relative to no treatment) is achieved by microwave heating in water, it is preferable to carry out the microwave heating step in an aqueous solution containing a heavy metal ion, particularly a divalent metal ion. Zinc and lead ions are particularly preferred, with lead ions generally producing the best results. The counter ion used is immaterial as long as a counter ion is selected that will provide solubility in water. Typical metal-ion solutions contain about 0.5–2% by weight of the salt. Concentrations of about 1% by weight are preferred.

The heating process is preferably carried out in a loosely covered container, as steam will sometimes be generated during the heating process and must be allowed to escape. On the other hand, completely open containers are not preferred, since a loose-fitting cover helps retain water during the heating process. A jar with a loose-fitting screw cap (or any container with a similar degree of "openness") is a preferred container in which to submerse the tissue preparation in the water for treatment.

A typical commercially available microwave oven can be used for the heating step. Alternatively, special equipment can be designed specifically for the process of the present invention. The microwave power setting will vary with the specific design of the equipment and the amount of material being treated. Microwaves are (by definition) in the frequency range of from 1 to 50 GHz. All commercially available microwave presently produce microwaves with a frequency of 2.45 GHz. Power levels are selected so as to provide between 300 to 800 W of power, preferably 600–750 W. At the optimal setting of 720 W, the temperature of 50 ml of water will increase at a rate of 1.67° C./second. Heating can be continuous or interrupted. For example, a 10-minute heating time can be divided into two 5-minute cycles with an interval of 1 minute between cycles in order to check on the fluid level in the containers during the heating process.

The total time that heating takes place can vary significantly. Even a relatively small amount of heating (a few seconds) improves antigen recovery in most cases. However, heating times of at least 1 minute are typical, preferably at least 5 minutes, more preferably about 10 minutes, usually less than 20 minutes, more generally less than 15 minutes.

The temperature at which heating takes place is generally that of the boiling point of the water or aqueous solution in which the heating takes place, although heating without reaching the boiling point is moderately effective. Since water boils at 100° C. (at 1 atmosphere of pressure), this is typically the temperature at which heating takes place in distilled water. With aqueous solutions, the boiling point is slightly elevated and depends on the concentration of the solution (as can be determined by Raoult'law). Solutions are generally sufficiently dilute so as not to raise the boiling point to more than 105° C.

After heating, containers with the immersed tissue preparation are removed from the microwave source and allowed to cool, e.g., for 15 min. The temperature to which the materials cool is not particularly important, except for ease of handling. However, the cooling process is useful as additional antigen retrieval continues during this time. After sufficient cooling to allow handling, the tissue preparations are usually rinsed with distilled water to remove any excess aqueous solution or metal salts from their surface. If they are heated in distilled water, no such rinsing is required However, a final rinsing in a buffer prior to immunological staining is preferred in order to provide physiological conditions suitable for antigen-antibody bonding on the surfaces of the tissue preparation. Buffers particularly provide a pH of 6.5 to 8.5, or preferably about 6.8 to 8.0, and most preferably about 7.0 to 7.6. Numerous physiological buffers are commercially available through biological supply houses. Specific buffers may be selected according to the antibody being used. Since such selection of buffers relates to the immunostaining process rather than to the antigen recovering process of the present invention, buffer selection is not considered to be a part of the present invention.

The immunological staining process is no different from that previously known. No modification of techniques is required for using an immunological staining process with the steps of the present invention described herein.

The invention now being generally described, the same will be better understood by reference to the following detailed examples, which are provided for purposes of illustration only and are not to be considered limiting of the invention unless so specified.

EXAMPLES

Preparation of Tissues and Paraffin Blocks

Fresh tissues were obtained from the Cooperative Human Tissue Network (CHTN, Columbus, Ohio) and were fixed immediately in either 10% neutral buffered formalin or 90% ethanol Fixed tissues were dehydrated in ethanol, cleared in xylene, and embedded into paraffin blocks. Some tissues, which had been fixed in formalin for from two weeks up to two years, were obtained from the Department of Pathology, National Medical Center of the City of Hope (Duarte, Calif.) and Hartford Hospital (Hartford, Conn.). Five-micron sections were cut and mounted on poly-L-lysine-coated slides. Poly-L-Lysine is a positively charged, high molecular weight polymer of the amino acid lysine which, when coated onto microscope slides, acts as a tissue adhesive bonding the tissue to the slide. The use of a tissue adhesive is a useful modification of this procedure as tissues are prone to detach from their slides upon exposure to high heat in aqueous solutions. Other tissue adhesive that could withstand microwave heating of slides are acceptable.

Sources of Reagents

All polyclonal and monoclonal antibodies listed in Table 1 were obtained from BioGenex Laboratories (San Ramon, Calif.). Unless otherwise specified the detection system for the immunohisto-chemical staining was the Super Sensitive system, also from BioGenex. In some experiments a MultLink Detection System (Biogenex) was also evaluated. Both horseradish peroxidase with AEC and alkaline phosphatase with Fast Red were used.

Standard Heating Step Using Microwave Oven

A Toshiba model ER-855BT operating at a frequency of 2.5 GHz with nine power level settings was used at the highest power setting (720 watts). Three Coplin jars were filled (50 ml each) with saturated lead thiocyanate, placed in the center of the microwave oven, and heated for two five-minute cycles with an interval of one minute between cycles. Because the number of Coplin jars placed in the microwave oven influences the temperature, three jars were always used and were always placed in the same positions in the following examples. However, in other tests using only one or two jars the process of antigen retrieval was similar to the results seen with three jars, even though the temperature increase was more rapid.

Standard Protocol for Antigen Retrieval

Although different antigens may behave differently under similar conditions of treatment, the following protocol was found to be acceptable for most antigens tested in this study. The steps for antigen retrieval were as follows:

1. Tissue sections were deparaffinized and rehydrated.
2. Endogenous peroxidase was blocked with 3% $H_2O_2$ for five minutes.
3. Slides were washed with distilled water for five minutes.
4. Slides were then placed in a plastic Coplin jar containing either distilled water, a metal solution of saturated lead thiocyanate, or 1% zinc sulfate.
5. Jars were covered with a loose fitting screw cap and heated in the microwave oven for either five or 10 minutes. Sometimes a 10-minute heating time was divided into two five-minute cycles with an interval of one minute between cycles in order to check on the fluid level in the jars.
6. After heating, the Coplin jars were removed from the oven and allowed to cool for 15 minutes.
7. Slides were then rinsed in distilled water twice and in PBS for five minutes.
8. Treated slides were immunostained as described below.

Immunohistochemistry

Immunohistochemical staining was performed according to the manufacturer's instructions. Briefly, all incubations were performed at room temperature as follows: 1) primary antibodies were incubated from 30 minutes to 24 hours according to the manufacturer's instructions, 2) link antibody was incubated for 20 minutes, 3) streptavidin-conjugated enzyme was incubated for 20 minutes, 4) peroxidase substrate was incubated for 5 minutes, or alkaline phophatase substrate was incubated for 20 minutes.

Enzyme Digestion

In some cases deparaffinized tissues were pretreated by protease digestion prior to application of the primary antibody. Tissue sections were incubated with 0.1% trypsin in phosphate buffer saline (PBS) for 30 minutes at 37° C. Following enzyme digestions, slides were rinsed in PBS and immunostained as previously described.

Nonimmune rabbit serum or nonspecific mouse ascites were used as negative controls for rabbit and mouse primary antibodies, respectively. Contribution of nonspecific staining of primary antibody was evaluated by substitution of the primary antibody with the negative controls or with PBS.

For comparison, a conventional oven was also used to heat the slides. The solutions were heated to the specified temperature and then the slides were placed in the preheated solutions for five to 10 minutes and then treated as previously described for the microwave procedure.

Results of Antigen Retrieval and Staining Processes

Immunostaining results using 52 different primary antibodies on tissues treated for antigen retrieval are summarized in Table 1. Most antibodies tested showed increased intensity of immunostaining following microwave oven heating in the presence of either distilled water or metal solutions. In general, the intensity of immunostaining was stronger with the metal solutions, particularly using the lead solution. Some cases, such as with monoclonal antibody to IgD, the use of zinc sulfate solution caused strong background staining of tonsil epithelium and some false positive staining of lymphocyte nuclei. This type of false positive staining was not observed with the lead solution.

TABLE 1

Immunostaining of Formalin-Fixed, Paraffin-Embedded Tissue Following Antigen Retrieval

| Improved Staining | No Change | Decreased Staining |
| --- | --- | --- |
| Pan-cytokeratin (F12-19) | Tubulin (P) | Ferritin (P) |
| Cytokeratin (AE1) | Desmin (P) | Ferritin |
| Cytokeratin (AE3) | Desmin (33) | (M3.170) |
| Cytokeratin (AE8) | Myoglobin (P) | C3 (P) |
| Cytokeratin 7 (CK7) | Myoglobin (MG-1) | Gastrin (P) |
| Cytokertain 8,18,19 (5D3) | β-Endorphin (P) | |
| IgD (IADB6) | α-1-Antitrypsin (P) | |
| GFAP (P) | Transferrin (HT1/13.6.3) | |
| GFAP (GA-5) | Calcitonin (P) | |
| NF (2F11) | | |
| CEA (P) | | |
| CEA (SP-651) | | |
| VIP (P) | | |
| Serotonin (P) | | |
| Estrogen receptor related protein (D5) | | |
| C-erb-B2 (CB11) | | |
| CMV (P) | | |
| Albumin (P) | | |
| Macrophage (LN5) | | |
| Blood group A (81 FR2.2) | | |
| Blood group B (81/11) | | |
| Cathepsin B (P) | | |
| Vimentin (V9) | | |
| NSE (P) | | |
| NSE (MIG-N3) | | |
| Chromogranin (LK3H10) | | |
| ACTH (R) | | |
| α-hCG (02-310-94) | | |
| PSA (8) | | |
| Thyroglobulin (P) | | |
| Factor VIII (P) | | |
| Myeloid, CD15 (Tü9) | | |
| T-cell (MT1) | | |
| T-cell (MT2) | | |
| B-cell (MB1) | | |
| B-cell (MB2) | | |
| Kappa chain (KP-53) | | |
| Lambda chain (HP6054) | | |
| AFP (A-013-01) | | |
| Total: 39 | 9 | 4 |

NOTE:
(P) = Polyclonal antibodies; others are monoclonal

Best results were obtained when slides were heated in the microwave oven using the intermittent heating method of two five minute cycles with an interval of one minute between the heating cycles. Another advantage of this method was that additional solution could be added to the jars if necessary.

Heating slides in distilled water or metal solutions by conventional heat in an oven also resulted in some increased immunostaining; however, there were noticeable differences (Table 2).

For tissues fixed in formalin for 24 hours or longer, heating the slides by microwave oven with or without metal solutions was clearly better than conventional heat with metal solutions although some enhanced staining was seen in the latter case. The intensity of positive immunostaining obtained by using conventional heat was consistently weaker than that obtained by microwave oven heat.

Sensitivity of Antigen Retrieval Method

In order to demonstrate the increased sensitivity achievable with this method, selected antibodies were tested at titers which failed to produce positive stains when tested by a conventional immunostaining procedure. Furthermore, immunoreactivity could not be demonstrated with these antibodies even with the use of trypsin pre-digestion of tissues. When these antibodies were then tested on the same tissues following antigen retrieval, strong immunostaining was observed (Table 3).

Specificity of the Angiten Retrivel Method

The specificity of the antigen retrieval method was tested by immunostaining tissues known to either contain or lack certain antigens. For these studies tissues were immunostained with monoclonal antibodies to cytokeratin 7 or estrogen-receptor related protein p29. Both of these antibodies detected formalin sensitive but ethanol resistant epitopes, Tissues were first categorized as being antigen positive or antigen negative by immunostaining frozen sections of each tissue fixed in ethanol. The remainder of the tissues were then fixed in formalin and embedded into paraffin. When paraffin-embedded tissues known to contain antigen were tested with antibody to cytokeratin 7, no staining occurred in any formalin-fixed tissue regardless of the length of time of fixation. Similarly with antibody to p29, no staining occurred in antigen-positive tissues which had been fixed in formalin for 48 hours or longer. Although neither antibody detected antigen in formalin fixed tissues prior to antigen retrieval, after retrieval both gave strong staining of their respective antigens. Furthermore, when formalin-fixed, paraffin-embedded tissues which were negative for these antigens were immunostained for cytokeratin 7 or p29, no staining occurred either with or without antigen retrieval.

Antigen Retrieval in Long-Term Formalin Fixed Tissues

Thirty-nine different tissues which had been fixed in formalin for periods of time ranging from 2-4 weeks and one tissue which had been stored in formalin for two years were tested for immunoreactivity to vimentin and pan-cytokeratin. As shown in Table 4, without treatment only a minority of the tissues were stained, and the staining that did occur was usually weak. However, following antigen retrieval with lead solution, immunoreactivity for these two antibodies was significantly enhanced, indicating that retrieval of antigen in long-term formalin fixed tissues was possible.

Effect of Formalin Fixation on Formalin Sensitive Antigens

A single sample of malignant melanoma was divided into several pieces, and each piece was fixed in formalin for 22 hours at temperatures of 4° C., 25° C., or 37° C. As the process of formalin fixation is temperature dependent, higher temperatures produce more rapid fixation (5). Following paraffin embedding, these tissues were subjected to immunostaining for vimentin. Because the epitope recognized by this vimentin antibody (clone V9) is partially formalin sensitive (27), this system was used to investigate whether antigen retrieval could be used to reverse the deleterious effects of fixation in formalin. As shown in Table 5, the observed decrease in vimentin immunoreactivity was directly related to an increase in temperature of the formalin fixative. However, following antigen retrieval in the presence of lead solution, vimentin immunostaining was completely restored to a level even surpassing that observed in tumor fixed at 4° C. without subsequent treatment (Table 5). These results indicate that, at least for some epitopes, the deleterious effects of formalin fixation are reversible.

Controls

For most antibodies diluted to their optimal titer, the signal-to-noise ratio was usually much better with tissues treated for antigen retrieval compared to untreated tissues, as the background was usually lower following antigen retrieval. However, in some tissues which were already prone to high background (staining in the absence of primary antibody), treatment by antigen retrieval further enhanced background staining. This type of background was associated with the direct binding of the secondary biotinylated antibody to the tissue and could usually be eliminated by appropriate dilution of the secondary antibody.

Alcohol Fixation

When antigen retrieval was performed on sections of tissues fixed by alcohol, there was no enhancement of immunoreactivity, whereas all sections fixed in 10% formalin, irrespective of the length of time of fixation, showed increased immunoreactivity.

Microwave oven treatment had no observable effects on tissue morphology when viewed by light microscopsy.

TABLE 2

Comparison of Conventional Heat to Microwave Heat for Antigen Retrieval in Overfixed Tissues

| Antibody[a] | Number of Tissues Tested | CONVENTIONAL OVEN | | | | MICROWAVE OVEN (Boiling) | |
|---|---|---|---|---|---|---|---|
| | | 80° C. | | Boiling | | | |
| | | H$_2$O | Lead | H$_2$O | Lead | H$_2$O | Lead |
| CK 8, 18, 19 | 2 | −[b] | + | ++ | +++ | +++ | +++++ |
| IgD | 2 | + | ++ | ++ | +++ | ++++ | +++++ |
| Pan-CK | 39 | + | ++ | +++ | ++++ | ++++ | +++++ |
| Vimentin | 39 | + | ++ | +++ | ++++ | ++++ | +++++ |

[a]Abbreviations used:
CK = Cytokeratin
[b]Immunoreactivity was scored on a scale of − to +++++. The reactivity score was an average value over all the tissues tested.

TABLE 3

A Comparison of Immunostaining Results Using Diluted Primary Antibodies

| Antibody Dilution | Tissues | Non-Treatment | Microwave[a] Oven | | | NC[b] | Trypsin Digestion |
|---|---|---|---|---|---|---|---|
| | | | DW | Zn | With Lead | | |
| Pan-K[c] | Tonsil | −[d] | ++ | +++ | +++ | − | − |
| CK AE1 | Tonsil | − | + | ++ | +++ | − | − |
| CK AE3 | Tonsil | − | ++ | +++ | +++ | − | − |
| CK AE8 | Tonsil | − | + | ++ | +++ | − | − |
| CK 7 | Adenocarcinoma[e] | − | ++ | ++ | +++ | − | +/− |
| IgD | Tonsil | − | ++ | + | +++ | − | − |

[a]Microwave oven with:
DW = distilled water,
Zn = Zinc sulfate solution,
Lead = lead thiocyanate
[b]NC: Negative control or PBS was used to replace primary antibody on the slide treated by microwave oven with metal solution or distilled water.
[c]CK = cytokeratin
[d]Immunoreactivity was scored on a scale of − to +++. The reactivity score was an average value taken over the entire tissue.
[e]Adenocarcinoma, breast adenocarcinoma.

TABLE 4

Immunoreactivity of Long-Term Formalin Fixed Tissues[a]

| Antibody | No Treatment | | Microwave + Lead | |
|---|---|---|---|---|
| | Antibody | NC[b] | Antibody | NC |
| Vimentin | 6/40[c] | 0/40 | 40/40 | 0/40 |

TABLE 4-continued

Immunoreactivity of Long-Term Formalin Fixed Tissues[a]

| | No Treatment | | Microwave + Lead | |
|---|---|---|---|---|
| Antibody | Antibody | NC[b] | Antibody | NC |
| Pan-CK[e] | 5/40 | 0/40 | 26/40[d] | 0/40 |

[a]Staining method was by the MultiLink alkaline phosphatase system.
[b]NC = Nonimmune ascites negative control.
[c]Represents the number of tissues staining positive (+ to +++) over the total number of the tissues treated.
[d]Of the 40 tissues tested only 26 contained epithelial cells which would be positive for kerative staining.
[e]CK = cytokeratin.

TABLE 5

Effect of Fixation Temperature on Vimentin Immunoreactivity in Malignant Melanoma

| Fixation[a] | No Treatment | | Microwave + Lead | |
|---|---|---|---|---|
| Temperature | Vimentin | NC[b] | Vimentin | NC |
| 4° C. | ++[c] | — | +++ | — |
| Pan-CK | 5/40 | — | +++ | — |
| 37° C. | — | — | +++ | — |

[a]Fixation in 10% neutral buffered formalin for 22 hours
[b]NC = nonimmune ascites negative control
[c]Immunoreactivity scored on a scale of — to +++

All publications and patent applications mentioned in this specification are herein incorporated by reference both the same extent as if each individual publication or patent application was specifically and individually indicated to be incorporated by reference.

The invention now being fully described, it will be apparent to one of ordinary skill in the t than many changes and modifications can be made thereto without departing from the spirit or scope of the appended claims.

What is claimed is:

1. A method for the preparation of formalin-fixed tissue for immunological staining, which comprises:
heating a formalin-fixed tissue preparation submersed in water with microwave energy for a time sufficient to increase immunostaining of said preparation in relation to immunostaining in the absence of said heating.

2. The method of claim 1, wherein said time is sufficient to boil said water.

3. The method of claim 1, wherein said water is an aqueous solution of a metal salt.

4. The method of claim 3, wherein said metal salt is a salt of lead or zinc.

5. The method of claim 2, wherein said water contains a dissolved metal salt and boils at a temperature at or above 100° C.

6. The method of claim 1, wherein said microwave energy has a frequency of from 1 to 50 GHz.

7. The method of claim 2, wherein said microwave energy is applied at a rate sufficient to cause 50 ml of said water to increase in temperature at a rate of from 0.5° to 5.0° C. per second prior to boiling.

8. The method of claim 2, wherein said boiling continues for up to 20 minutes.

9. The method of claim 3, wherein said method further comprises removing said tissue preparation from said water after being subjected to said microwave energy and washing to remove said aqueous solution.

10. A method of immunologically staining a formalin-fixed tissue preparation, which comprises:
(a) subjecting a formalin-fixed tissue preparation or tissue section on a microscope slide to microwave energy while said tissue preparation is submersed in water for a time sufficient to boil said water;
(b) removing said tissue preparation from said water and cooling to a temperature below 100° C.; and
(c) contacting said tissue preparation with an immunological staining reagent or series of reagents.

11. The method of claim 10, wherein said water is an aqueous solution of a metal salt.

12. The method of claim 11, wherein said metal salt is a salt of lead or zinc.

13. The method of claim 11, wherein said water contains a dissolved metal salt and boils at a temperature above 100° C.

14. The method of claim 10, wherein said microwave energy has a frequency of from 1 to 50 MHz.

15. The method of claim 10, wherein said microwave energy is applied at a rate sufficient to cause 50 ml of said water to increase in temperature at a rate of from 0.5° to 5° C. per second prior to boiling.

16. The method of claim 10, wherein said boiling continues for up to 20 minutes.

17. The method of claim 10, wherein said tissue preparation is stained with an enzyme-labelled monoclonal antibody.

18. The method of claim 10, wherein said tissue preparation is first reacted with an unlabeled monoclonal or polyclonal antibody and subsequently reacted with a reagent or series of reagents to introduce an enzyme label at the site of the antigen-antibody reaction.

* * * * *